United States Patent
Madhat

(12)
(10) Patent No.: US 6,264,974 B1
(45) Date of Patent: Jul. 24, 2001

(54) BUCCAL AND SUBLINGUAL ADMINISTRATION OF PHYSOSTIGMINE

(76) Inventor: Maher N. Madhat, 3305 Grasmere Dr., Lexington, KY (US) 40503

(*) Notice: Subject to any disclaimer, the term of this patent is extended or adjusted under 35 U.S.C. 154(b) by 0 days.

(21) Appl. No.: 09/111,550

(22) Filed: Jul. 7, 1998

(51) Int. Cl.$^7$ ...................................... A61F 13/00
(52) U.S. Cl. .......................... 424/434; 424/435; 424/441; 424/464; 424/468; 424/472; 424/474; 424/484; 514/411
(58) Field of Search .................... 424/434, 435, 424/441, 464, 468, 472, 474, 484; 514/411

(56) References Cited

U.S. PATENT DOCUMENTS

| | | | |
|---|---|---|---|
| 2,698,822 | 1/1955 | Halpiern et al. | 167/65 |
| 3,444,858 | 5/1969 | Russell | 128/260 |
| 3,632,743 | 1/1972 | Giellar et al. | 424/45 |
| 3,870,790 | 3/1975 | Lowey et al. | 424/19 |
| 3,972,995 | 8/1976 | Tsuk et al. | 424/28 |
| 4,020,558 | 5/1977 | Coornut et al. | 32/40 R |
| 4,229,447 | 10/1980 | Porter | 424/244 |
| 4,259,314 | 3/1981 | Lowey | 424/19 |
| 4,278,667 | 7/1981 | Madison et al. | 424/232 |
| 4,432,975 | 2/1984 | Libby | 424/201 |
| 4,539,315 | 9/1985 | Benoer et al. | 514/162 |
| 5,073,374 | * 12/1991 | McCarty | 424/435 |
| 5,472,958 | * 12/1995 | Gunn, Jr. et al. | 514/210 |
| 5,591,452 | 1/1997 | Miller et al. | 424/468 |
| 5,686,094 | * 11/1997 | Acharya | 424/434 |

FOREIGN PATENT DOCUMENTS

| | | |
|---|---|---|
| 0069600 A2 | 1/1983 | (EP) . |
| 2108841A | 5/1983 | (GB) . |
| 2108841 | * 5/1983 | (GB) . |

OTHER PUBLICATIONS

Clinical Pharmacokinetics of Physostigmine in Patients with Alzheimer's Disease, Sanjay Asthana, MD. et al., Clinical Pharmacology & Therapeutics, Sep. 1995, pp. 299–309.

Development of a Trans–Mucosal Controlled–Release Device for Systemic Delivery of Anti Anginal Drugs Pharmacokinetics and Phrnaco–Dynamics, K. Yukimatsu et al., Drug Development & Industrial Pharmacy, 20(4), pp. 503–534, 1994.

Enhancement of Memory Process in Alzhiemer's Disease with Multiple–Dose Intravenous Physostigmine, Kenneth L. Davis, M.D. et al., Am. J. Psychiatry, 139:11, Nov. 1982, pp. 1421–1424.

Buccal Morphine—A New Route For Analgesia, M.D.D. Bell et al, the Lancet, Jan. 12, 1985, pp. 71–73.

(List continued on next page.)

*Primary Examiner*—Gollamudi S. Kishore
*Assistant Examiner*—Lakshmi Channavajjah

(57) ABSTRACT

Physostigmine, 1,2,3,3a,8,8a-hexahydro-1,3a,8-trimethylpyrrolo[2,3-b] indol-5ol methylcarbamate, administered buccally or sublingually in non-sustained release dosage form provides extremely prolonged blood levels. This active agent is physically compounded with materials of some or all of classes of ingredients that function as pH controls, preservative agents, viscosity control agents, absorption enhancers, stabilizing agents, solvents, and carrier vehicles. This compounding will produce a pharmaceutical composition in the form of a liquid, tablet, gel, patch or lozenge for administration of the active agent, Physostigmine, by absorption through the buccal or sublingual mucosa of the patient. This method of delivery of Physostigmine and similar compounds is useful for treatment of cognitive deficiencies and/or neurological function deficits, mood and/or mental disturbances in mammals including human beings.

4 Claims, 1 Drawing Sheet

OTHER PUBLICATIONS

Morphine and Metabolite Behavior After Different Routes of Morphine Administration: Demonstration of the Importance of the Active Metabolite Morphine–6–Glucuronide, Richard Osborne, MD et al., Clinical Pharmacol. Ther., Jan. 1990, pp. 12–19.

Haemodynamics and Plasma Concentrations Following Sublingual GTN and Intervenous, or Inhaled, Isosorbide Dinitrate, W. Culling et al. Br. J. Clin. Pharmac., (1984) vol. 17, pp. 125–131.

Effects of Acute Buprenorphine on Responses to Intranasal Cocaine: a Pilot Study, Marc I. Rosen et al, Am. J. Drug Alcohol Abuse, vol. 19(4), pp. 451–464, (1993).

International Conference on Radioative Isotopes In Pharmacology, P.G. Waser et al., p. 447. 1972.

Modern Pharmaceutics, Third Edition, edited by Gilbert S. Banker and Christopher T. Rhodes, p. 547 1996.

Remington's Pharmaceutical Sciences, 1985, p. 1278 and p. 1803.

* cited by examiner

BUCCAL AND SUBLINGUAL ADMINISTRATION OF PHYSOSTIGMINE

FIELD OF INVENTION

This invention relates to a method of administration of Physostigmine, a known effective treatment for improving cognition in Alzheimer Disease patients and which may have a use for nerve gas poisoning, and a composition of materials which permits administration of Physostigmine through the membranes of the mouth, buccally or sublingually, for attaining sustained blood levels of this active agent.

BACKGROUND OF THE INVENTION

This invention relates to pharmaceutical compositions containing cholinesterase inhibitors, in particular Physostigmine, suitable for buccal or sublingual administration. The oral administration/ingestion of Physostigmine and other cholinesterase inhibitors elicits in the patient a substantially lesser response as compared to an equal dosage administrated parenterally. The lower plasma concentration and resulting reduced efficacy resulting from oral administration most commonly results from the extensive metabolism of the drug during transit from the gastrointestinal tract to the general circulation system. For example, an orally administered drug must pass through the intestinal mucosa and the liver, both of which are abundant in enzymes that will rapidly and effectively metabolize the drug in many ways, thereby reducing the plasma concentration of Physostigmine and its effectiveness to a very short period of time following the oral administration.

Whenever an orally administered drug such as Physostigmine is metabolized rapidly by the gastrointestinal system or liver prior to entering the general circulation, the drug's bioavailability is greatly reduced. This metabolic breakdown of the active drug may be circumvented by administering the drug by an alternative route. Examples of such alternative routes include buccal or sublingual administration. Drugs administered by these routes avoid gut-wall and hepatic metabolism, thereby producing increased bioavailability as compared to oral administration. Neither buccal nor sublingual administration of Physostigmine is known from the prior publications or patents, nor is a beneficial sustained release plasma profile found in prior publications or patents.

It was suggested by K. L. Davis et al. in the Am. J. Psych., 139 (11): 1421–1424, (1982), that until there is a long term administration method maintaining sustained drug plasma concentrations for cholinomimetics (cholinesterase inhibitors) such as Physostigmine in Alzheimer patients, they will be difficult to clinically utilize.

Suitable nontoxic pharmaceutically acceptable carriers for use in the composition of the present buccal or sublingual dosages can be found in Remington's Pharmaceutical Sciences, 17th Edition, 1985. Lozenges for buccal or sublingual administration are described in Modem Pharmaceutics, edited by G. S. Banker and C. T. Rhodes, 1996.

Although there are other compounds absorbed through the buccal/sublingual mucosa, they do not provide a sustained/controlled release plasma profile. For Physostigmine, heretofore, a sustained plasma profile has required a continuous intravenous infusion which is inconvenient and impractical for chronic therapy.

A number of prior publications disclose buccal or sublingual administration of drugs of various types. G. F. Blane et al., in International Conference on Radioactive Isotopes in Pharmacology, 1969, disclose the absorption of etorphine and dihydromorphine from the buccal cavity. D. Bell, M.D., et al. in The Lancet, 1(8420), 71–73, 1985, disclose buccal administration of morphine sulfate. R. S. Todd in British Patent GB2,100,985, published Jan. 12, 1983, discloses a pharmaceutical composition for the sublingual administration of buprenorphine and salts thereof. H. Lowey in U.S. Pat. No. 4,259,314, issued Mar. 31, 1981, discloses a lozenge for buccal administration of dextromethorphan.

A number of other references disclose formulations and delivery systems for buccal administration, including Coumut and Guassens in U.S. Pat. No. 4,020,558, issued May 3, 1977; Porter in U.S. Pat. No. 4,229,447, issued Oct. 21, 1980; Tsuk in U.S. Pat. No. 3,972,995, issued Aug. 3, 1976; Lowey et al. in U.S. Pat. No. 3,870,790, issued Mar. 11, 1975; Russell in U.S. Pat. No. 3,444,858, issued May 20, 1969; Halpern et al. in U.S. Pat. No. 2,698,822, issued Jan. 4, 1955; Geller et al. in U.S. Pat. No. 3,632,743, issued Jan. 4, 1972; and Kissel et al. in United Kingdom Patent Application GB 2,108,841A, published May 25, 1983.

Bender et al, in U.S. Pat. No. 4,539,315, issued Sep. 3, 1985, discloses an aspirin composition for sublingual administration; Libby in U.S. Pat. No. 4,432,975, issued Feb. 21, 1984, discloses a microlozenge containing vitamin B-12 for sublingual administration.

Other publications that have discussed buccal/sublingual administration of drugs include: Culling et al., in the Br. J. Clin. Pharm. 17, 125–131, 1984, disclosing the sublingual administration of the glyceryl trinitrate; Osborne et al., published in the Clin. Pharmac. Ther. 47, 12–19, 1990, on buccal administration of morphine; Rosen et al., published in the Am. J. Drug Alcohol Abuse, 19, 451–464, 1993, on the sublingual administration of Buprenorphine.

In all the cited studies, buccal and sublingual administration provided drug plasma concentrations that were not significantly sustained and decayed with profiles similar to that observed after either parenteral or oral administration.

K. Yukimatsu et al, published in the Drug Dev. and Ind. Pharmacy, 20(4), 503–534, 1994, Development Of A Transmucosal Controlled Release Devices For Systemic Delivery Of Antianginal Drugs. These devices require that the dosage form stays in the mouth for a long period of time, which is obviously impractical due to physiological needs such as eating and drinking. Furthermore, S. Asthana et al. suggested in the Clin. Pharmac. And Therap., 58 (3) 1995, that sustained delivery of Physostigmine is the most effective way of delivering this drug. The sustained delivery technique discussed by Asthana et al. was by continuous intravenous infusion. The drawback to the continuous intravenous infusion is the impracticality of this technique whenever continuous and long term administration is indicated.

OBJECTS OF THE INVENTION

The primary object of the invention is to provide a method for the delivery of drugs for improved effectiveness to treat Alzheimer's disease patients.

Another object of the invention is to provide a method for the delivery of drugs for improved effectiveness for treatment of nerve gas poisoning.

A still another object of the invention is to provide prolonged stable blood levels of Physostigmine and similar compounds.

A further object of the invention is to provide a sustained plasma levels of Physostigrnine in patients.

Yet another object of the invention is to provide an improved long term administration method for delivering Physostigmine to Alzheimer's patients and to people exposed to nerve gas poisoning.

An additional object of the invention is to eliminate the need for a continuous intravenous infusion of cholinesterase inhibitors for the treatment of chronic cognitive deficiencies.

Other objects and advantages of the present invention will become apparent from the following descriptions, taken in connection with the accompanying formula wherein, by way of illustration and example, a preferred embodiment of the present invention is disclosed.

SUMMARY OF THE INVENTION

The foregoing objects of the Invention are accomplished and the problems and shortcomings associated with prior art administration techniques and approaches are overcome by the incorporation of the drug Physostigmine into a composition to be administered buccally or sublingually.

According to the present invention, a method of delivering Physostigmine or similar cholinesterase inhibitor compounds for the treatment of Alzheimer's Disease or nerve gas poisoning, either buccally or sublingually, is disclosed. This new treatment technique and delivery method unexpectedly results in a prolonged and sustained plasma concentration of the active drug in mammals using formulations that are not necessarily sustained release delivery systems.

Compounds suitable for delivery using this method include Physostigmine, 1,2,3,3a,8,8a-hexahydro-1,3a,8-trimethylpyrrolo[2,3-b]indol-5-ol methylcarbamate, or a salt thereof, and structurally similar compounds. As used above, the term "salt thereof" is meant to include any nontoxic pharmaceutically suitable salt of a compound described above with the desired pharmacological properties in mammals. Preparation of such a salt is well-known to those skilled in pharmaceutical science. Pharmaceutically acceptable acid addition salts of the above compounds include: hydrochloride, hydrobromide, hydroiodide, sulfate, bisulfate, nitrate, salicylate, citrate, tartarate, bitartarate, lactate, phosphate, malate, maleate, fumarate, succinate, acetate and pamoate. Acid forms thereof. Also suitable for buccal/sublingual delivery or administration using this method are other cholinesterase inhibitors such as Metrifonate, Donepezil, and structurally similar compounds.

A better and more complete understanding of the invention may be garnered from the drawings and detailed description of the preferred embodiment of the best mode of the invention as contemplated by the inventor.

Figure 1:
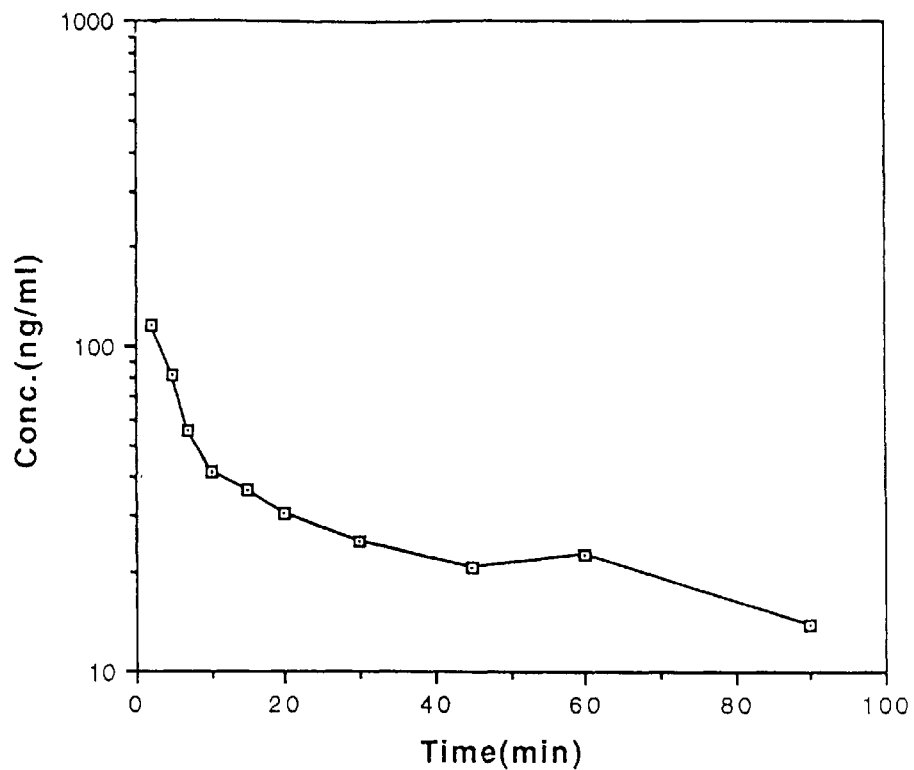
FIG. 1 is a plasma concentration versus time profile for an intravenously administered dose of Physostigmine in rats.

DETAILED DESCRIPTION OF THE BEST MODE OF THE PREFERRED EMBODIMENTS OF THE INVENTION AS CONTEMPLATED BY THE INVENTOR

Detailed descriptions of the preferred embodiment are provided herein; however, it is to be understood that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Compounds of the present invention incorporating Physostigmine or structurally similar active ingredients can be administered buccally or sublingually to treat cognitive or neurological dysfunction including Alzheimer's Disease patients or as a treatment for nerve gas poisoning using any pharmaceutically suitable formulation that results in the active agent reaching the agent's sites of action in the body of mammals and particularly humans. The benefits of the Physostigmine have been previously established or evidenced by its approval by the United States Food and Drug Administration and its placement on the approved drug list for the treatment of Alzheimer's Disease patients.

Physostigmine and structurally similar active ingredients are drugs of the formula:

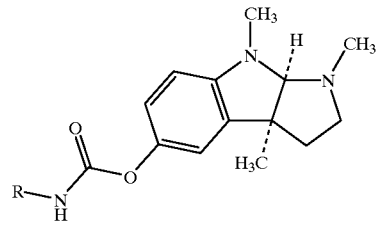

where R is a carbon chain having from 1–10 carbon atoms. This invention provides a delivery technique for administration of Physostigmine, a generic drug, to the patient through the mucous membranes of the mouth, buccally/sublingually, in a non-sustained release dosage form while obtaining and providing plasma concentrations of Physostigmine that are extremely sustained, simulating a slow intravenous infusion. The acetylcholinesterase inhibitors in general, and specifically Physostigmine, can be administered buccally or sublingually either as an individual agent or in combination with other therapeutic agents such as muscarinic agonists or neurotransmitter release enhancers. These drugs generally are administered with a pharmaceutical carrier selected on the basis of the chosen formulation and standard pharmaceutical practices. Whenever a dosage that is not in a solution form is used, the carrier dissolves in the saliva to release and expose the active drug Physostigmine to the mucosa of the mouth for absorption thereby.

The administered dose of the cholinesterase inhibitor will vary depending upon known factors such as: the pharmacodynamic characteristics of the particular agent; the age, health and weight of the recipient; the nature and extent of symptoms; the kind of concurrent treatment; frequency of treatment; and the effect desired. Usually a daily buccal or sublingual dosage of drug can be about 0.001 to 1.0 mg/kg of body weight while the preferred dosage range is about 0.001–0.01 mg/kg given either once a day or in divided doses 2 to 4 times a day, to provide a more consistent plasma level of the drug.

The active ingredients can be administered buccally or sublingually by preparing a suitable formulation of the active ingredient and utilizing procedures well known to those skilled in the art. Preferably, the formulations are prepared with suitable nontoxic pharmaceutically acceptable ingredients. These ingredients are known to those skilled in the preparation of buccalisublingual dosage forms; some of these ingredients can be found in Remington's Pharmaceutical Sciences, 17th edition, 1985, a standard reference in the field. The choice of suitable carriers is highly dependent upon the exact nature of the buccal/sublingual dosage form desired, e.g. solutions, sprays, drops, gels, tablets, pastes, patches, or lozenges.

The compounding of ingredients identified in Remington's Pharmaceutical Sciences may include minor amounts of other ingredients such as pH adjusters, emulsifiers or dispersing agents, preservatives, surfactants, gelling agents, as well as buffering and other stabilizing and solubilizing agents.

EXAMPLE I

An example of a buccal or sublingual solution of this invention is:

| Physostigmine salt (active drug) | 100 mg | Powder |
|---|---|---|
| Citric acid | as a buffer | as needed to create buffered solution |
| Sodium citrate | as a buffer | as needed to create buffered solution |
| Sodium bisulfite | 50 mg | as antioxidant |
| Benzyl alcohol | 200 mg | as a preservative |
| Sodium chloride | | as needed for tonicity |
| Sodium hydroxide | | as needed to adjust the pH to about pH 5 |
| Hydrochloric acid | | as needed to adjust the pH to about pH 5 |
| Purified water | | to a total solution volume of 100 ml |

The solution may be administered by drops in the buccal cavity or sprayed into the mouth periodically.

The vehicle solution is prepared by dissolving the appropriate amounts of citric acid, sodium citrate, sodium bisulfite, benzyl alcohol and sodium chloride in purified water; and the desired pH is obtained either by adding sodium hydroxide or hydrochloric acid. Physostigmine salt then is added at the desired concentration to 95% of the volume of the vehicle solution, with stirring. The pH is checked and adjusted if needed. The volume then is adjusted to 100% using the vehicle solution and packaged in the desired packaging configuration.

EXAMPLE II

Another solution example:

| Physostigmine salt (active drug) | 100 mg | |
|---|---|---|
| Sodium bisulfite | 50 mg | antioxidant |
| Benzyl alcohol | 100 mg | preservative |
| Purified water | as needed to produce a total solution volume up to 100 ml | |

The formulation of this invention may be varied to include:
1) acids and bases to adjust the pH;
2) tonicity imparting agents such as sorbitol, glycerin and dextrose;
3) antimicrobial preservatives, to inhibit microbial contamination, such as other parahydroxybenzoic acid esters (sorbate, benzoate, propionate), chlorobutanol, benzyl alcohol, benzalkonium chloride, and mercurials;
4) other viscosity imparting agents such as sodium carboxymethylcellulose, microcrystalline cellulose, polyvinylpyrrolidone, polyvinyl alcohol and other gums;
5) suitable absorption enhancers, such as surfactants, bile acids;
6) stabilizing agents such as antioxidants, like bisulfites and ascorbates; metal chelating agents, such as sodium edetate; and drug solubility enhancers, such as polyethylene glycols. These additional ingredients help make commercial solutions with adequate stability so that they need not be compounded on demand.

Liquid formulations, such as either of the above formulations, can be administered as drops, spray, aerosols or by any other dosage form. Optionally, the delivering system can be a unit dose delivery system. The volume of solution or suspension delivered per dose can be anywhere from 5 to 400 µl, preferably between 50 to 150 µl. Delivery systems for these various dosage forms can be dropper bottles, plastic squeeze units, atomizers, nebulizers, pharmaceutical aerosols in either unit dose or multiple dose packages.

EXAMPLE III

An example of a fast dissolving tablet is:

| Physostigmine salt (active drug) | 1% by weight | in powdered form |
|---|---|---|
| Mannitol | 98.5% by weight | soluble carrier in powder form |
| Magnesium sterate | 0.5% by weight | as a lubricant |

The mixture is blended and mixed to form a paste which then may be formed, using a die and pressure, into a tablet.

EXAMPLE IV

An example of a buccal patch is:

| Physostigmine salt | 1% by weight |
|---|---|
| Klucel ® EF | 89% by weight |
| Carbopol ® | 5% by weight |
| PBG 400 | 5% by weight |

The first three ingredients are dry powders which are triturated with PEG 400 in a mortar and pestle. After forming a uniform mixture, the resulting composition is pressed in a hydraulic press onto a carrier film and the patches are cut. The carrier film preferably will be longer lasting in saliva than the Physostigmine compound. The carrier may be insoluble, if desired, but must be removed and discarded after use.

Klucel® EF is available from B.F. Goodrich, Cleveland, Ohio. Carbopol® is available from Hercules, Wilmington, Del. PEG 400, a polyethylene glycol is available from Sigma, St. Louis, Mo.

TESTING EXAMPLE

Lewis Rats were used to evaluate the buccal/sublingual delivery of Physostigmine. The Physostigmine drug concentration in rat plasma was determined using a conventional high pressure liquid chromatography analytical procedure which measures drug concentration by fluorimetric detector.

To determine whether Physostigmine would be absorbed by mucosa and produce a sustained plasma level, two separate groups of male Lewis rats, were administered Physostigmine hemisulfate, a salt of Physostigmine, intravenously or buccally in normal saline. The rats weighed approximately 300 g and were fasted overnight prior to dosing. All rats were anesthetized with pentobarbital (50 mg/kg) prior to dosing. The jugular vein was cannulated and attached to a syringe through 3-way stopcock for blood collections. Blood samples (1 ml) were withdrawn through the jugular cannula and replaced with an equal volume of fresh blood (37 degrees C) from separate blood donor rats after each sampling as a function of time.

In the instances of intravenous administration, the dose was equivalent to 200 µg/kg body weight of Physostigmine, in a volume of 1 ml/kg body weight, injected through the femoral vein.

For buccal administration, the same 200 µg/kg body weight dose used for i.v. was administered in a volume of 0.25 ml/kg body weight. Buccal dosing was performed on rats in which the esophagus was ligated through a small incision on the neck, and then the incision was closed using surgical staples. This ligation prevented the dosing solution from being swallowed. Rats were maintained on their abdomen with their jaw on the surface of the bench. The dosing solution was applied but not injected into the mucosa between the cheek and lower gum with a syringe and blunt needle.

The blood samples for testing were collected into heparinized test tubes containing 50 µl of 100 µ/ml solution of neostigmine bromide (as a stabilizer for Physostigmine). Plasma was separated immediately and frozen for storage. Analysis of the plasma Physostigmine was performed using a previously reported method described by Brodie et al., 1987, in J. Chromatogr. Apr. 10; 715 (2) 423–431.

INTRAVENOUS AND BUCCAL PHARMACOKINETICS

Figure 2:
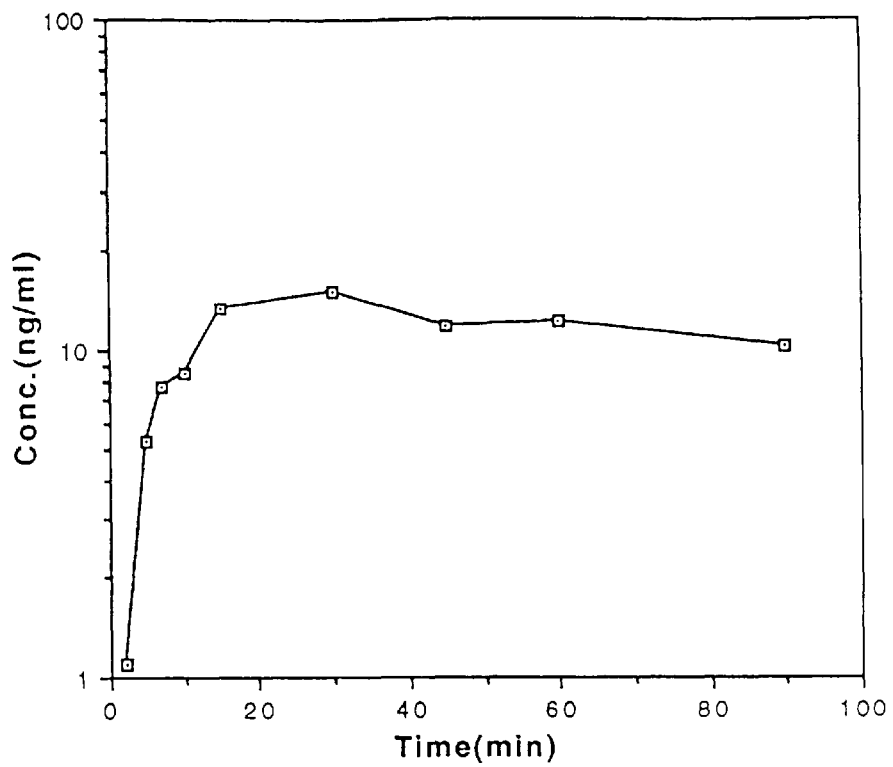
FIG. 2 is a plasma concentration versus time profile of a buccally or sublingually administered dose of Physostigmine in rats.

Plasma levels after intravenous and buccal administrations are shown in FIGS. 1 and 2, respectively. The terminal decay rate constant (k) and the terminal half-life ($t_{1/2}$) after intravenous administration was calculated by linear regression of the terminal portion of the individual sample In Cp (plasma drug concentration) versus time plot of FIG. 1.

However, since the plasma concentration did not decay for the period of the experiment, $t_{1/2}$ could not be determined for buccal dosing, as can be observed in FIG. 2.

Physostigmine plasma half-life after intravenous administration was very short (25 min.); consistent with that reported by S. Asthana et al. (Clin. Pharmac. And Therap., 58 (3) 1995); however, after buccal dosing, the plasma concentrations of Physostigmine were highly sustained such that a half-life ($t_{1/2}$) could not be determined over a period of eight hours. This plasma concentrations vs. time profile is illustrated in FIG. 2.

The advantage of buccal/sublingual dosing of Physostigmine is that such dosing provides sustained plasma concentrations of Physostigmine that would be difficult if not impossible to attain and sustain by methods other than slow intravenous infusion, which is impractical for chronic therapy with these drugs.

The formulation of Physostigmine used was not a sustained or slow release formulation (aqueous solution) and was not expected to produce a sustained plasma level; but with administration by buccal or sublingual techniques and compounds for such administration, the benefits of a prolonged or sustained release administration are unexpectedly achieved.

While the invention has been described in connection with preferred embodiments, it is not intended to limit the scope of the invention to the particular form set forth; but, on the contrary, it is intended to cover such alternatives, modifications, and equivalents as may be included within the spirit and scope of the invention as defined by the appended claims.

I claim:

1. A method of buccal or sublingual administration of Physostigmine for achieving prolonged plasma concentrations of said Physostigmine in a mammal comprising the steps of: preparing a solution of said Physostigmine or a salt thereof dissolved in an aqueous carrier solution; disposing the said solution, containing physostigmine or a salt thereof, within a sublingual or buccal cavity of said mammal in a quantity to deliver a dosage of 0.001 to 1.0 mg/kg of body weight of said mammal; and absorbing said Physostigmine or salt thereof into buccal or sublingual mucosa, thereby creating and maintaining prolonged plasma concentrations of said Physostigmine for at least 90 minutes.

2. A method of claim 1 wherein said dosage of Physostigmine or a salt thereof is 0.001 to 0.01 mg/kg of body weight.

3. A method of treatment of cognition or neurological dysfunction in a mammal comprising the steps of: preparing a mixture comprising an active agent in an aqueous carrier, wherein a said active agent is selected from the group consisting of Physostigmine or a salt thereof, and other compounds having formula 1:

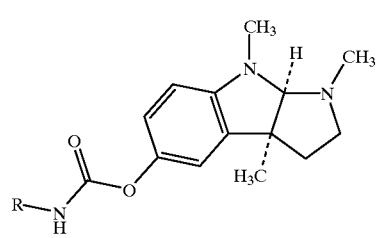

Formula 1

Where R is a carbon chain having from 1 to 10 carbon atoms, and administering said mixture buccally or sublingually, said mixture being in the form of a spray or solution thereby resulting in prolonged plasma concentration of said active agent for at least 90 minutes.

4. A method of claim 1 wherein the aqueous carrier solution further comprises:

Tonicity imparting agents;

Preservatives, viscosity imparting agents, absorption enhancers, stabilizing agents, metal chelating agents, and drug solubility enhancers.

* * * * *